United States Patent
Yamaki et al.

(10) Patent No.: US 11,801,207 B2
(45) Date of Patent: *Oct. 31, 2023

(54) WATER-IN-OIL EMULSION SUNSCREEN COSMETIC

(71) Applicant: SHISEIDO COMPANY, LTD., Tokyo (JP)

(72) Inventors: Satoshi Yamaki, Yokohama (JP); Kazutaka Sasaki, Yokohama (JP); Takashi Matsui, Yokohama (JP); Yurika Watanabe, Yokohama (JP); Mayuri Tashiro, Yokohama (JP); Yuko Nagare, Yokohama (JP); Marianne Ayaka Touati, Yokohama (JP); Kazuhiro Yamaguchi, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/522,016

(22) PCT Filed: Oct. 30, 2015

(86) PCT No.: PCT/JP2015/080764
§ 371 (c)(1),
(2) Date: Apr. 26, 2017

(87) PCT Pub. No.: WO2016/068298
PCT Pub. Date: May 6, 2016

(65) Prior Publication Data
US 2017/0333301 A1 Nov. 23, 2017

(30) Foreign Application Priority Data

Oct. 31, 2014 (JP) ................................ 2014-222962
Oct. 9, 2015 (JP) ................................ 2015-201594

(51) Int. Cl.
| | | |
|---|---|---|
| *A61Q 17/04* | (2006.01) | |
| *A61K 8/06* | (2006.01) | |
| *A61K 8/40* | (2006.01) | |
| *A61K 8/60* | (2006.01) | |
| *A61K 8/73* | (2006.01) | |
| *A61K 8/25* | (2006.01) | |
| *A61K 8/27* | (2006.01) | |
| *A61K 8/37* | (2006.01) | |
| *A61K 8/894* | (2006.01) | |
| *A61K 8/49* | (2006.01) | |
| *A61K 8/44* | (2006.01) | |
| *A61K 8/895* | (2006.01) | |
| *A61K 8/36* | (2006.01) | |
| *A61K 8/58* | (2006.01) | |

(Continued)

(52) U.S. Cl.
CPC ................ *A61K 8/064* (2013.01); *A61K 8/06* (2013.01); *A61K 8/25* (2013.01); *A61K 8/27* (2013.01); *A61K 8/36* (2013.01); *A61K 8/37* (2013.01); *A61K 8/40* (2013.01); *A61K 8/44* (2013.01); *A61K 8/49* (2013.01); *A61K 8/585* (2013.01); *A61K 8/60* (2013.01); *A61K 8/73* (2013.01); *A61K 8/8129* (2013.01); *A61K 8/891* (2013.01); *A61K 8/894* (2013.01); *A61K 8/895* (2013.01); *A61Q 17/04* (2013.01); *A61K 2800/48* (2013.01); *A61K 2800/522* (2013.01)

(58) Field of Classification Search
CPC ...... A61K 8/064; A61K 8/585; A61K 8/8129; A61K 8/891; A61K 2800/48; A61Q 17/04
See application file for complete search history.

(56) References Cited

U.S. PATENT DOCUMENTS 5,389,363 A * 2/1995 Snyder .................... A61K 8/585
424/401
6,159,452 A * 12/2000 Stewart .................... A61K 8/35
424/59

(Continued)

FOREIGN PATENT DOCUMENTS

EP 1 283 031 A2 2/2003
JP A-HEI 1180237 7/1989

(Continued)

OTHER PUBLICATIONS

Glenn Corp., "ABIL® EM 90, Emulsifier for the formulation of cosmetic W/O creams and lotions," Evonik Industries, published Apr. 2008, p. 1-7.*
PCT/JP2015/080764, International Search Report and Written Opinion, dated Feb. 2, 2016, 3 pages—English, 9 pages—Japanese.
Ishii, Hiroaki, et al., Efficacy and Physical Properties of Sunscreen Film, Oleoscience, 2009, vol. 9, No. 5, p. 183-188, ISSN: 1345-8949.
EP 15854207.6, Search Report dated May 4, 2018, 7 pages—English.
JP 2016-556661, Notice of Reasons for Refusal, dated Aug. 23, 2019, 7 pages—Japanese, 7 pages—English.

(Continued)

*Primary Examiner* — Jyothsna A Venkat
(74) *Attorney, Agent, or Firm* — Andrew F. Young; NOLTE LACKENBACH SIEGEL

(57) ABSTRACT

The object is providing a water-in-oil emulsion sunscreen cosmetic having a property not present in the prior art, in which UV protection ability improve upon contact with water, sweat and the like in comparison with that directly after application, and also having pleasant texture and easy to wash off. The present invention provides a water-in-oil emulsion sunscreen cosmetic comprising (A) 6 to 40 mass % of a UV protective agent; (B) an organic-modified clay mineral; (C) an oil-phase-thickening agent, other than (B) and (D) a silicone-based surfactant having an HLB of less than 8, wherein the ratio, [total quantity of component (B) and component (C)]/[total quantity of (E) non-volatile liquid oils except silicone oils], is 0.04 or more and less than 0.68.

2 Claims, No Drawings

(51) Int. Cl.
*A61K 8/81* (2006.01)
*A61K 8/891* (2006.01)

(56) References Cited

U.S. PATENT DOCUMENTS

| | | | | |
|---|---|---|---|---|
| 7,563,452 B2* | 7/2009 | Kuroda | ................. | A61K 8/585 |
| | | | | 424/401 |
| 2005/0079188 A1* | 4/2005 | Ohmori | ................. | A61K 8/39 |
| | | | | 424/401 |
| 2008/0145436 A1* | 6/2008 | Lorant | ................. | A61K 8/064 |
| | | | | 424/489 |
| 2009/0098169 A1* | 4/2009 | Ootake | ................. | A61K 8/06 |
| | | | | 424/401 |
| 2010/0172850 A1* | 7/2010 | Mitsui | ................. | A61K 8/11 |
| | | | | 424/59 |
| 2012/0196942 A1 | 8/2012 | Yamaguchi et al. | | |
| 2012/0201905 A1* | 8/2012 | Mune | ................. | A61K 8/19 |
| | | | | 424/684 |
| 2012/0269875 A1 | 10/2012 | Tamura et al. | | |
| 2012/0288458 A1 | 11/2012 | Yamaguchi et al. | | |
| 2013/0121939 A1 | 5/2013 | Fukuhara | | |
| 2014/0010775 A1 | 1/2014 | Sonoyama et al. | | |
| 2014/0205552 A1 | 7/2014 | Fukuhara | | |

FOREIGN PATENT DOCUMENTS

| | | |
|---|---|---|
| JP | H1-180237 | 7/1989 |
| JP | A HEI 8217619 | 8/1996 |
| JP | H8-217619 | 8/1996 |
| JP | H08217618 | 8/1996 |
| JP | H09255543 | 9/1997 |
| JP | 9-301823 | 11/1997 |
| JP | 10-513188 | 12/1998 |
| JP | 2000-63233 | 2/2000 |
| JP | 2000063233 | 2/2000 |
| JP | 2000063233 A * | 2/2000 |
| JP | JP 2000063233 | 2/2000 |
| JP | 2000-72646 | 3/2000 |
| JP | 2001187711 | 7/2001 |
| JP | 2002-193741 | 7/2002 |
| JP | 2004-083541 | 3/2004 |
| JP | 2004-83541 | 3/2004 |
| JP | 2004-83541 A | 3/2004 |
| JP | 2004091374 | 3/2004 |
| JP | 2005053846 | 3/2005 |
| JP | 2006-306868 A | 11/2006 |
| JP | 2007-217380 | 8/2007 |
| JP | 2007-332295 | 12/2007 |
| JP | 2007332295 | 12/2007 |
| JP | 2009-40738 | 2/2009 |
| JP | WO2011049248 | 3/2011 |
| JP | 2011-126832 | 6/2011 |
| JP | 2011-126832 A | 6/2011 |
| JP | 2011111401 | 6/2011 |
| JP | 2011126832 | 6/2011 |
| JP | 2011126832 A * | 6/2011 |
| JP | 2011-153079 | 8/2011 |
| JP | 2011-153079 A | 8/2011 |
| JP | 2012-188-394 | 10/2012 |
| JP | 2012-197241 | 10/2012 |
| JP | 2012197241 | 10/2012 |
| JP | 2012-219029 | 11/2012 |
| JP | 2013-209342 A | 10/2013 |
| JP | 2013209342 | 10/2013 |
| JP | 2014-88346 A | 5/2014 |
| JP | 2014088369 | 5/2014 |
| JP | 2014-222962 | 10/2014 |
| JP | 2014201541 | 10/2014 |
| JP | 2014224075 | 12/2014 |
| JP | 2015-201594 | 10/2015 |
| KR | 10-2003-0027644 | 4/2003 |
| RU | 2297826 | 4/2007 |
| WO | WO2009/119000 | 10/2009 |
| WO | WO 2011/049248 | 4/2011 |
| WO | WO 2011/093018 | 8/2011 |
| WO | PCT/JP2015/080764 | 10/2015 |

OTHER PUBLICATIONS

RU 2017116842/04, Russian Office Action dated May 14, 2019, 7 pages—Russian, 5 pages—English.
PCT/JP2017/014935 International Search Report and Written Opinion, dated Jul. 4, 2017, 3 pages—English, 10 pages—Japanese.
U.S. Appl. No. 16/095,457, Office Action dated Apr. 1, 2019, 8 pages.
U.S. Appl. No. 15/765,012, Office Action dated Apr. 17, 2019, 12 pages.
PCT/JP2016/079962, International Search Report and Written Opinion, dated Dec. 20, 2016, 2 pages—English, 11 pages—Japanese.
Notice of Reasons for Revocation dated Nov. 14, 2018, 28 pages—English.
Fragrance Journal 1999-5, Rayleigh, Proc. Roy Soc. 84A; Kingerty W.O. Bowen, H.K. and Uhlman, 1 page—English, 5 pages—Japanese (pp. 79-83).
Tamura Takeo "Cosmetics Science" (issued 3$^{rd}$ Edition, Jun. 10, 1978), Japan Society of Hair Sciences 122-125 (Annex 9), 4 pages—Japanese; 2 pages—English.
U.S. Appl. No. 15/764,738, Office Action dated Sep. 23, 2019, 11 pages.
U.S. Appl. No. 15/764,738, Response to Office Action dated Dec. 13, 2019, 9 pages.
JP 2016-556661, Decision of Rejection, dated Mar. 24, 2020, 5 pages—Japanese, 5 pages—English.
EP 15 854 207.6 Office Action dated Nov. 11, 2020, 4 pages.
JP 6742911, Notification of Reasons for Revocation dated Jun. 7, 2021, 18 pages—Japanese; 18 pages—English.
JP 2020-106940, Notice of Reasons for Rejection dated Jul. 29, 2021, 8 pages—Japanese; 10 pages—English.
JP 2020-106940, Notice of Reasons for Rejection/Office Action dated Aug. 3, 2021—8-pages Japanese; 7 pages English.
KR 2017-7011987, Korean Office Action dated May 31, 2022, 7 pages—Korean, 8 pages—English.

\* cited by examiner

WATER-IN-OIL EMULSION SUNSCREEN COSMETIC

CROSS REFERENCE TO RELATED APPLICATIONS

This application relates to and claims priority as a § 371 national phase, from PCT/JP2015/080764 filed Oct. 30, 2015, the entire contents of which are incorporated herein by reference, which in turn claims priority from JP 2014-222962 filed Oct. 31, 2014, and which also claims priority form JP 2015-201594 filed Oct. 9, 2015.

TECHNICAL FIELD

The present invention relates to a water-in-oil emulsion sunscreen cosmetic. More specifically, the present invention relates to a water-in-oil emulsion sunscreen cosmetic whose UV protection ability improves upon contacting with water, sweat, or the like in comparison with that directly after application, which is a novel property not present in conventional water-in-oil emulsion sunscreen cosmetics. Furthermore, the water-in-oil emulsion sunscreen cosmetic of the present invention also provides an excellent texture and can be easily washed off.

BACKGROUND ART

Protection of the skin from harmful effects of ultraviolet rays is one of the major issues in skin care and body care, and various sun care cosmetics have been developed to minimize adverse effects of ultraviolet rays on the skin. A sunscreen cosmetic, which is one of sun care cosmetics, blocks the arrival of UVA and UVB to the skin with a UV absorbing agent or UV-scattering agent blended therein, and thus protects the skin from harmful effects of ultraviolet rays (Non Patent Document 1). In recent years, protection of the skin from ultraviolet rays has been considered important, not only under severe UV conditions in outdoor activities such as bathing in a pool or the ocean in the summer and skiing in the winter, but also in daily life, and even normal skin care products are desired to have a UV protection ability.

When a sunscreen cosmetic applied on the skin contacts water or sweat, however, the UV absorbing agent or UV-scattering agent tends to elute from the applied cosmetic, and the UV protection ability is inevitably degraded. To prevent such degradation of UV protection ability, various attempts have been made such as improvement of the water resistance or film strength of sunscreen cosmetics.

Patent Document 1 discloses, for example, a water-in-oil emulsion composition containing a water-swellable clay mineral, a quaternary ammonium salt-type cationic surfactant, a polyoxyalkylene-modified organopolysiloxane, an aqueous phase, and an organic silicone resin represented by the general formula $R_nSiO_{(4-n)/2}$, and argues that blending the organic silicone resin improves the water resistance and water repellency, and thus the UV absorbing agent is retained on the skin for a long time.

Patent Document 2 also discloses a water-in-oil emulsion cosmetic which contains a UV-protective agent, an organic-modified clay mineral, a volatile component, a spherical resin powder, and a film-forming agent, and argues that blending the film-forming agent prevents the powder from being peeled off upon rubbing or from secondarily attaching to clothes.

Since a cosmetic applied on the skin is exposed to various types of moisture from the inside and outside of the cosmetic film, e.g., sweat secreted from the skin and moisture from the exterior environment such as sea water, however, it is difficult to completely prevent elution of the UV absorbing agent, UV-scattering agent, or the like, even when a larger quantity of a resin or film-forming agent to impart water resistance is blended. Moreover, it has been considered impossible to achieve a UV protection higher than that directly after application, even if elution of the UV absorbing agent or the like could be completely prevented.

On the other hand, there are problems different from those relating to UV protection ability may be arise when a large quantity of a silicone resin, film-forming agent, or the like is blended in a cosmetic. Specifically, such a cosmetic causes, after being applied, a strong film-like feeling, which result in poor texture, and the cosmetic is poorly spread upon application, and cannot be easily washed off with a usual cleansing agent or soap, which requires use of a special cleansing agent.

BACKGROUND ART DOCUMENTS

Patent Document

Patent Document 1: JP-A-Hei 1-180237
Patent Document 2: JP-A-Hei 8-217619
Non Patent Document 1: "Shin Keshyohin Gaku" ("New cosmetology", in English), 2nd edition, Mitsui Takeo ed., 2001, NANZANDO Co., Ltd., p. 497-504

SUMMARY OF THE INVENTION

Problem to be Solved by the Invention

In the course of study to develop a sunscreen cosmetic having potent UV protection ability, the present inventors found a phenomenon that the UV protection ability is not degraded but rather improves on contact with water, sweat, or the like. On the basis of the finding, an object of the present invention is to provide a sunscreen cosmetic, whose UV protection improves upon contact with moisture, which is a novel and innovative property not present in conventional sunscreen cosmetics.

Means for Solving the Problem

The present inventors diligently investigated to solve the above problems, and found that a sunscreen cosmetic having the intended novel property can be obtained by blending an organic-modified clay mineral and an oil-phase-thickening agent at a specific mass ratio to non-volatile liquid oils except silicone oils, and thus completed the present invention.

The present invention provides a water-in-oil emulsion sunscreen cosmetic comprising:
(A) 6 to 40 mass % of a UV protective agent;
(B) an organic-modified clay mineral;
(C) an oil-phase-thickening agent, other than (B); and
(D) a silicone-based surfactant having an HLB of less than 8,
wherein the ratio, [total quantity of component (B) and component (C)]/[total quantity of (E) non-volatile liquid oils except silicone oils], is 0.04 or more and less than 0.68.

Effects of the Invention

In the present invention, the above configuration significantly improves the UV protection ability after contact with water, sweat, or the like, in comparison with that directly after application of the cosmetic on the skin. That is, the water-in-oil emulsion sunscreen cosmetic according to the present invention is an innovative sunscreen cosmetic the UV protection of which improves on contact with moisture, which is a property exactly contrary to the common general knowledge because contact with moisture has been considered to be a cause for degradation of the UV protection ability in conventional sunscreen cosmetics.

Further, the sunscreen cosmetic according to the present invention exerts excellent UV protection even without a larger quantity of a silicone resin, film-forming agent, or the like, and thus causes no film-like feeling, well spreads (upon application), and can be easily washed out with a usual cleansing agent or soap. In short, the present invention can provide a water-in-oil emulsion sunscreen cosmetic which provides excellent texture and cleansability, in addition to having a unique UV protection ability.

MODES FOR CARRYING OUT THE INVENTION

As mentioned above, the water-in-oil emulsion sunscreen cosmetic according to the present invention contains: 6 to 40 mass % of a (A) UV protective agent; (B) an organic-modified clay mineral; (C) an oil-phase-thickening agent other than (B); and (D) a silicone-based surfactant having an HLB of less than 8, wherein the ratio ([total quantity of component (B) and component (C)]/[total quantity of (E) non-volatile liquid oils except silicone oils]) is 0.04 or more and less than 0.68. Hereinafter, the components constituting the sunscreen cosmetic according to the present invention will be described in detail.

(A) UV Protective Agent

The UV protective agent, (A), (hereinafter, occasionally referred to as "component (A)") to be blended in the water-in-oil emulsion sunscreen cosmetic according to the present invention consists of at least one selected from UV absorbing agents and UV scattering agents, which are usually blended in a conventional sunscreen cosmetic.

The UV absorbing agent used in the present invention is not specifically limited, and examples thereof include organic UV absorbing agents such as ethylhexyl methoxycinnamate, octocrylene, dimethicodiethyl benzalmalonate, polysilicone-15, t-butylmethoxydibenzoylmethane, ethylhexyl triazone, hexyl diethylaminohydroxybenzoylbenzoate, bis-ethylhexyloxyphenol methoxyphenyl triazine, oxybenzone-3, methylene bis-benzotriazolyl tetramethylbutyiphenol, phenylbenzimidazolesulfonic acid, homosalate, and ethylhexyl salicylate.

The UV scattering agent used in the present invention is not specifically limited, and examples thereof include fine particles of metal oxides such as zinc oxide, titanium oxide, iron oxide, cerium oxide, and tungsten oxide.

The UV scattering agent may be a non-surface-treated one or a one subjected to various surface hydrophobizing treatments. Among them, the UV scattering agents having a hydrophobized surface are preferable. The examples of applicable surface-hydrophobizing agents include those common in the field of cosmetics, such as dimethicone, silicones such as alkyl-modified silicones, alkoxysilanes such as octyltriethoxysilane, dextrin fatty acid esters such as dextrin palmitate, and fatty acids such as stearic acid. Among them, a UV-scattering agent surface-treated with an alkoxysilane such as octyltriethoxysilane is particularly preferred because of its good cleansability.

The blend ratio of component (A) to the total quantity of the water-in-oil emulsion sunscreen cosmetic is 6 to 40 mass %, and preferably 7 to 30 mass %. If the blend ratio of component (A) is less than 6 mass %, it is difficult to achieve sufficient UV protection ability. If the blend ratio of component (A) is more than 40 mass %, an enhanced UV protection ability matching the blend ratio could not be expected, and such a quantity is not preferred from the viewpoint of, for example, deterioration of the stability.

The UV protective agent (component (A)) in the present invention is at least one selected from a UV absorbing agent and a UV scattering agent. The present invention encompasses an embodiment in which the UV protective agent consists only of a UV absorbing agent, an embodiment in which the UV protective agent consists only of a UV scattering agent, and an embodiment in which the UV protective agent consists of both a UV absorbing agent and a UV scattering agent.

Each of the above numerical ranges is represented as the total blend ratio of a UV absorbing agent and a UV scattering agent, and it is particularly preferred to set the blend ratio of a UV absorbing agent to 6 mass % or more.

(B) Organic-Modified Clay Mineral

The organic-modified clay mineral, (B), (hereinafter, occasionally referred to as "component (B)") is one of colloidal hydrous aluminum silicates having a tri-layer structure, and a substance derived by modification of a clay mineral represented by the following general formula (1) with a quaternary ammonium salt-type cationic surfactant can be used for compound (B):

$$(X,Y)_{2-3}(Si,Al)_4O_{10}(OH)_2Z_{1/3} \cdot nH_2O \tag{1}$$

where, X=Al, Fe(III), Mn(III), or Cr(III), Y=Mg, Fe(II), Ni, Zn, or Li, and Z=K, Na, or Ca.

Specific examples are obtained by treating a clay mineral such as a natural or synthetic (in this case, an (OH) group in the formula is substituted with a fluorine) substance belonging to the montmorillonite group including montmorillonite, saponite, and hectorite (commercial products: VEEGUM, Kunipia, LAPONITE, etc.) and a synthetic mica known as sodium silicic mica or sodium or lithium taeniolite (commercial product: Dimonite from TOPY INDUSTRIES LIMITED, etc.) with a quaternary ammonium salt-type cationic surfactant.

The quaternary ammonium salt-type cationic surfactant to be used here is represented by the following general formula (2):

(2)

where, $R^1$ denotes a $C_{10-22}$ alkyl group or a benzyl group; $R^2$ denotes a methyl group or a $C_{10-22}$ alkyl group; $R^3$ and $R^4$ each denote a $C_{1-3}$ alkyl group or a hydroxyalkyl group; and X denotes a halogen atom or a methylsulfate residue.

Examples of such quaternary ammonium salt-type cationic surfactants include dodecyltrimethylammonium chloride, myristyltrimethylammonium chloride, cetyltrimethylammonium chloride, stearyltrimethylammonium chloride, arachyltrimethylammonium chloride, behenyltrimethylammonium chloride, myristyldimethylethylammonium chloride, cetyldimethylethylammonium chloride, stearyldimethylethylammonium chloride, arachyldimethylethylammonium chloride, behenyldimethylethylammonium chloride, myristyldiethylmethylammonium chloride, cetyldiethylmethylammonium chloride, stearyldiethylmethylammonium chloride, arachyldiethylmethylammonium chloride, behenyldiethylmethylammonium chloride, benzyldimethylmyristylammonium chloride, benzyldimethylcetylammonium chloride, benzyldimethylstearylammonium chloride, benzyldimethylbehenylammonium chloride, benzylmethylethylcetylammonium chloride, benzylmethylethylstearylammonium chloride, and dibehenyldihydroxyethylammonium chloride, and bromides corresponding to them, and dipalmityipropylethylammonium methylsulfate. In implementation of the present invention, one or two or more of them are arbitrarily selected.

Representative examples of component (B) include dimethyldistearammonium hectorite (disteardimonium hectorite), dimethylalkylammonium hectorite, benzyldimethylstearylammonium hectorite, and magnesium aluminum silicate treated with distearyldimethylammonium chloride. Among them, dimethyldistearammonium hectorite is particularly preferred. Preferred commercial products are Bentone 27 (hectorite treated with benzyldimethylstearylammonium chloride, manufactured by Elementis Japan K.K.) and Bentone 38 (hectorite treated with distearyldimethylammonium chloride, manufactured by Elementis Japan K.K.).

The blend ratio of component (B) to the total quantity of the water-in-oil emulsion sunscreen cosmetic is 0.1 to 3 mass %, preferably 0.2 to 2 mass %, and more preferably 0.4 to 1 mass %. If the blend ratio of component (B) is less than 0.1 mass %, it is difficult to achieve sufficient stability. If the blend ratio of component (B) is more than 3 mass %, the viscosity becomes higher and the cosmetic poorly spreads on the skin, for example, and thus such a quantity is not preferred from the viewpoint of the texture.

(C) Oil-Phase-Thickening Agent

The oil-phase-thickening agent, (C), (hereinafter, occasionally referred to as "compound (C)") is a component capable of adjusting the viscosity of the oil phase but other than component (B). The (C) oil-phase thickening agent is preferably a dextrin fatty acid ester, a sucrose fatty acid ester, or a fatty acid or a salt thereof, for example, and it is particularly preferred to blend two or more selected from them.

The dextrin fatty acid ester is an ester of dextrin or reduced dextrin and a higher fatty acid, and any dextrin fatty acid ester commonly used for cosmetics may be used without any limitation. Preferably used is dextrin or reduced dextrin having an average degree of saccharide polymerization of 3 to 100. It is preferred to use a saturated $C_{8-22}$ fatty acid for the fatty acid constituting a dextrin fatty acid ester. Specific examples thereof include dextrin palmitate, dextrin oleate, dextrin stearate, dextrin myristate, and dextrin (palmitate/2-ethylhexanoate).

A sucrose fatty acid ester in which the fatty acid is a linear or branched, saturated or unsaturated, $C_{12-22}$ fatty acid can be preferably used. Specific examples thereof include sucrose caprylate, sucrose caprate, sucrose laurate, sucrose myristate, sucrose palmitate, sucrose stearate, sucrose oleate, and sucrose erucate.

Any fatty acid being solid at normal temperature may be used, and examples thereof include myristic acid, palmitic acid, stearic acid, and behenic acid. Examples of salts of a fatty acid include calcium salts, magnesium salts, and aluminum salts of the fatty acids.

The blend ratio of component (C) to the total quantity of the water-in-oil emulsion sunscreen cosmetic is 0.1 to 15 mass %, preferably 0.2 to 10 mass %, and more preferably 0.4 to 8 mass %. If the blend ratio of component (C) is less than 0.1 mass %, it is difficult to achieve sufficient stability. If the blend ratio of component (C) is more than 15 mass %, the viscosity becomes higher and the cosmetic poorly spreads on the skin, for example, and thus such a quantity is not preferred from the viewpoint of the texture.

(D) Silicone-Based Surfactant Having HLB of Less than 8

The silicone-based surfactant, (D) (hereinafter, occasionally referred to as "component (D)") is not limited and may be any silicone-based surfactant having a silicone skeleton (polysiloxane structure) and an HLB of less than 8. Preferred is use of a polyoxyalkylene-modified silicone, a polyoxyalkylene/alkyl-comodified silicone, a polyglycerin-modified silicone, and/or a polyglycerin/alkyl-comodified silicone. Among them, a polyoxyalkylene-modified silicone and a polyoxyalkylene/alkyl-comodified silicone are more preferred.

The polyoxyalkylene-modified silicone used in the present invention has a main skeleton of a linear or branched organopolysiloxane and a side chain of a polyoxyalkylene group, and examples thereof include those represented by the following general formula (3).

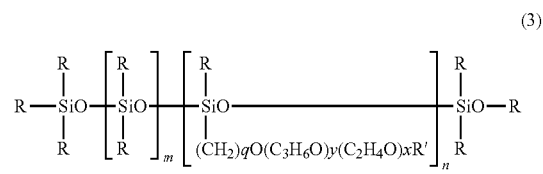

(3)

In the general formula (3), R denotes a $C_{1-3}$ alkyl group or a phenyl group (preferably, a methyl group); R' denotes a hydrogen or a $C_{1-12}$ alkyl group (preferably, a hydrogen or a methyl group); q is 1 to 50 (preferably, 3); m is 1 to 100; n and x are each 1 to 50; and y is 0 to 50. Preferred examples of such polyoxyalkylene-modified silicones include KF-6017 (PEG-10 dimethicone, manufactured by Shin-Etsu Chemical Co., Ltd.).

In the formula (3), the organopolysiloxane main skeleton may have another organopolysiloxane chain as a side chain. Preferred examples of such polyoxyalkylene-modified silicones include KF-6028 (PEG-9 polydimethylsiloxyethyl dimethicone, manufactured by Shin-Etsu Chemical Co., Ltd.).

The polyoxyalkylene/alkyl-comodified silicone used in the present invention has a liner or branched main skeleton of an organopolysiloxane and side chains of a polyoxyalkylene group and alkyl group having four or more carbon atoms, and examples thereof include those represented by the general formula (4).

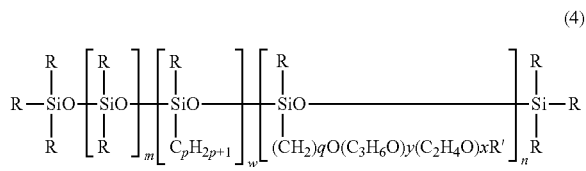

(4)

In the general formula (4), R denotes a alkyl group or a phenyl group (preferably, a methyl group); R' denotes a hydrogen or a $C_{1-12}$ alkyl group (preferably, a hydrogen); p is 6 to 30 (preferably, 10 to 18, particularly preferably 12 to 16); q is 1 to 50 (preferably, 3); m is 1 to 100; n, w, and x are each 1 to 50; and y is 0 to 50. Preferred examples of such polyoxyalkylene/alkyl-comodified silicones include ABIL EM90 (cetylPEG/PPG-10/1 dimethicone, manufactured by Evonik Goldschmidt GmbH).

In the general formula (4), the organopolysiloxane main skeleton may have another organopolysiloxane chain as a side chain. Preferred examples of such polyoxyalkylene/alkyl-modified silicones include KF-6038 (lauryl PEG-9 polydimethylsiloxyethyl dimethicone, manufactured by Shin-Etsu Silicone).

Examples of polyglycerin-modified silicones include linear polyglycerin-modified silicones (=polyglycerin siliconized at both ends) represented by the following formula (5):

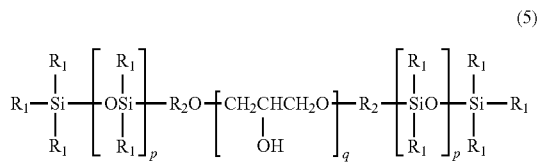

where, $R_1$ denotes a linear or branched $C_{1-12}$ alkyl group or a phenyl group; $R_2$ denotes a $C_{2-11}$ alkylene group; p is 10 to 120; and q is 1 to 11. Specific examples of such polyglycerin-modified silicones include bis-butyldimethicone polyglyceryl-3.

The polyglycerin/alkyl-comodified silicone has a main skeleton of a linear or branched organopolysiloxane and side chains of a polyglycerin group and alkyl group having four or more carbon atoms, and examples thereof include KF-6105 (lauryl polyglyceryl-3 polydimethylsiloxyethyl dimethicone, manufactured by Shin-Etsu Chemical Co., Ltd.).

The blend ratio of component (D) to the total quantity of the water-in-oil emulsion sunscreen cosmetic is 0.1 to 8 mass %, preferably 0.2 to 7 mass %, and more preferably 0.4 to 5 mass %. If the blend ratio of component (D) is less than 0.1 mass %, it is difficult to achieve sufficient stability. If the blend ratio of component (D) is more than 8 mass %, the viscosity is higher and the cosmetic poorly spreads on the skin, for example, and thus such a quantity is not preferred from the viewpoint of usability.

(E) Non-Volatile Liquid Oils Except Silicone Oils

The cosmetic according to the present invention is a water-in-oil emulsion cosmetic, and inevitably contains an oil component constituting the outer phase (continuous phase). The oil component in the present invention contains non-volatile liquid oils and may further contain a volatile oil.

In the present specification, a "non-volatile liquid oil component" refers to a liquid oil which does not exhibit volatility at normal temperature (25° C.) and normal pressure (1 atm ($9.8 \times 10^4$ Pa)) (including oils having a boiling point of 200° C. or higher at normal pressure), and exhibits fluidity and is not solid at normal temperature and under normal pressure, and encompasses non-volatile silicone oils and non-volatile oils other than silicone oils (such as hydrocarbon oils, ester oils, etc.).

In the present invention, non-volatile liquid oils except silicone oils are referred to as component (E), and component (E) includes an oily UV absorbing agent corresponding to component (A). Accordingly, the (E) non-volatile liquid oils except silicone oils may consist only of a UV absorbing agent.

Examples of non-volatile liquid oils belonging to component (E) and not belonging to the UV absorbing agent include hydrocarbon oils, vegetable oils, ester oils, and polyalkyleneglycols with high molecular weight.

Specific examples thereof include liquid fats and oils such as linseed oil, *camellia* oil, macadamia nut oil, corn oil, olive oil, avocado oil, sasanqua oil, castor oil, safflower oil, apricot kernel oil, cinnamon oil, jojoba oil, grapeseed oil, almond oil, rapeseed oil, sesame oil, sunflower oil, wheat germ oil, rice germ oil, rice bran oil, cottonseed oil, soybean oil, peanut oil, tea seed oil, evening primrose oil, egg-yolk oil, cod-liver oil, triglycerin, glyceryl trioctanoate, and glyceryl triisopalmitate; ester oils such as octanoates such as cetyl octanoate, isooctanoates such as glyceryl tri-2-ethylhexanoate and pentaerythrite tetra-2-ethylhexanoate, laurates such as hexyl laurate, myristates such as isopropyl myristate and octyldodecyl myristate, palmitates such as octyl palmitate, stearates such as isocetyl stearate, isostearates such as isopropyl isostearate, isopalmitates such as octyl isopalmitate, oleates such as isodecyl oleate, adipates such as diisopropyl adipate, sebacates such as diethyl sebacate, and diisostearyl malate; hydrocarbon oils such as liquid paraffin and squalane; and polyoxybutylene polyoxypropylene glycol.

The volatile oil blendable in the cosmetic according to the present invention includes a volatile hydrocarbon oil and a volatile silicone oil.

The volatile hydrocarbon oil is not limited and may be any volatile hydrocarbon oil which is conventionally used in cosmetics and has volatility at normal temperature (25° C.). Specific examples thereof include isododecane, isohexadecane, and hydrogenated polyisobutene.

Examples of the volatile silicone oil include silicone oils which are conventionally used for cosmetics and each have volatility at normal temperature such as volatile linear silicone oils (volatile dimethicone) and volatile cyclic silicone oils (volatile cyclomethicone). Examples of applicable volatile dimethicones include low-viscosity dimethylpolysiloxanes such as decamethyltetrasiloxane, and examples of commercial products thereof include KF-96L-1.5cs and KF-96L-2cs (each manufactured by Shin-Etsu Chemical Co., Ltd.). Examples of volatile cyclomethicones include decamethylcyclopentasiloxane (Execol D-5 manufactured by Shin-Etsu Silicone Co., Ltd).

In the cosmetic according to the present invention, it is preferred to blend a volatile oil, in particular, a volatile silicone oil, in the oil component. The blend ratio of the volatile oil is not limited, and typically is approximately 1 to 40 mass %.

Ratio[total quantity of component(*B*) and component (*C*)]/[total quantity of(*E*)non-volatile liquid oils except silicone oils]

The water-in-oil emulsion sunscreen cosmetic according to the present invention is required to have a specific ratio of the total quantity of component (B) and component (C), both of which involve in viscosity adjustment of the oil phase, to the total quantity of (E) non-volatile liquid oils except silicone oils.

Specifically, the ratio [total quantity of component (B) and component (C)]/[total quantity of (E) non-volatile liquid oils except silicone oils] (hereinafter, occasionally represented as "ratio of oil-phase-thickening agents") must be 0.04 or more and less than 0.68, and the ratio is preferably 0.045 or more and less than 0.5. If the ratio is less than 0.04 or 0.68 or more, the UV protection ability does not improve upon contact with moisture.

(F) Oil-Soluble Film Forming Agent

In the present invention, (F) an oil-soluble film forming agent, (hereinafter, occasionally referred to as "component (F)") may be blended in addition to the components (A) to (E). Component (F) blended can further enhance the resistance of (A) UV protective agent to elution or peeling off due to rubbing with a cloth or the like.

Component (F) is not limited and may be any oil-soluble film forming agent conventionally used in cosmetics, and specific examples thereof include polyvinylpyrrolidone (PVP)-based film forming agents such as PVP, PVP/dimethylaminoethyl methacrylate copolymers, PVP/eicosene copolymers, PVP/ethyl methacrylate/methacrylic acid copolymers, PVP/hexadecene copolymers, PVP/VA copolymers, PVP/vinyl acetate/itaconic acid copolymers, and styrene/PVP copolymers; acrylic film forming agents such as ethyl acrylate/acrylamide/acrylic acid copolymers, ethyl acrylate/butyl acrylate copolymers, ethyl acrylate/ethyl methacrylate copolymers, ethyl acrylate/methacrylic acid copolymers, ethyl acrylate/methyl methacrylate copolymers, octyl acrylate/vinyl acetate copolymers, octyl acrylate/styrene copolymers, butyl acrylate/vinyl acetate copolymers, butyl acrylate/hydroxy ethyl methacrylate copolymers, butyl acrylate/methyl methacrylate copolymers, methoxyethyl acrylate/hydroxyethyl acrylate/butyl acrylate copolymers, lauryl acrylate/vinyl acetate copolymers, polyethyl acrylate, polybutyl acrylate, and polystyrene acrylate resins; vinyl acetate-based film forming agents such as polyvinyl acetate; methacrylate-based film forming agents such as polymethyl methacrylate, methyl methacrylate/butyl acrylate/octyl acrylate, and vinylpyrrolidone diethylsulfate/N,N'-dimethylaminomethacrylic acid copolymers; vinyl methyl ether-based film forming agents such as vinyl methyl ether/ethyl maleate copolymers and vinyl methyl ether/butyl maleate copolymers; styrenic film forming agents such as styrene/methylstyrene/indene copolymers; alkyd resin film forming agents such as cyclohexane-based alkyd resins; and silicone resin film forming agents such as trimethylsiloxysilicate. Among them, trimethylsiloxysilicate is preferred from the viewpoint of water resistance and oil resistance.

In the case that component (F) is blended, the blend ratio of component (F) is preferably a blend ratio such that the ratio [quantity of component (F) blended]/[total quantity of non-volatile liquid oils except silicone oils, (E)] (hereinafter, occasionally represented as "ratio of film forming agents") is less than 0.5. If the ratio is 0.5 or more, the film-like feeling becomes stronger, and the texture or cleansability tends to be deteriorated. Although the lower limit of the ratio of film forming agents is not limited, the ratio of film forming agents is preferably 0.01 or more to achieve a sufficient effect of blending of the film forming agent.

(G) Polyoxyethylene-Polyoxypropylene Dialkyl Ether

In the present invention, (G) polyoxyethylene-polyoxypropylene dialkyl ether (herein after, occasionally referred to as "component (G)") may be further blended in addition to components (A) to (F).

Component (G) is a dialkyl ether of a random or block copolymer of polyoxyethylene and polyoxypropylene, and specific example thereof include polyoxyethylene (14)-polyoxypropylene (7) random copolymer dimethyl ether. The blend ratio of component (G) to the total quantity of the water-in-oil emulsion sunscreen cosmetic is preferably 0.001 to 5 mass %.

(H) Spherical Resin Powder

Blending a spherical resin powder (hereinafter, occasionally referred to as "component (H)") in the cosmetic according to the present invention further improves the texture and provides a smooth and good feeling.

The spherical resin powder usable in the present invention is not limited and any spherical resin powder conventionally used for cosmetics may be used arbitrarily. Examples thereof include (meth)acrylate resin powders, polyamide resin powders (nylon powders), polyethylene powders, polystyrene powders, resin powders of a copolymer of styrene and (meth)acrylic acid, benzoguanamine resin powders, polytetrafluoroethylene powders, cellulose powders, and trimethylsilsesquioxane powders (hereinafter, the above powders are referred to as "spherical organic resin powder"); and spherical powders of organopolysiloxane elastomer (including powders of methylsiloxane network polymer) or composite spherical powders including spherical powders of organopolysiloxane elastomer as base powders (hereinafter, the above powders are referred to as "spherical silicone resin powder"). The particle diameter, etc., of the spherical resin powder to be blended is not limited, and a spherical powder having a particle diameter of approximately 1 to 50 μm is suitably used, for example. The resin powder may be hydrophobized in advance.

Examples of commercially available spherical organic resin powders include GANZPEARL (manufactured by Aica Kogyo Co., Ltd.), and examples of commercially available spherical silicone resin powders include TREFIL E-505C, TREFIL E-506C, TREFIL E-506S, and TREFIL HP40T (each manufactured by Dow Corning Toray Silicone Co., Ltd.), Tospearl 145A (manufactured by Toshiba Silicone Co., Ltd.), and Silicone Powders KSP-100 and KSP-300 (manufactured by Shin-Etsu Chemical Co., Ltd.).

In the present invention, one or two or more of these spherical resin powders may be arbitrarily selected for use. The blend ratio of component (H) in the cosmetic according to the present invention is not particularly limited.

In addition to the above-described components, a component conventionally used in cosmetics may be appropriately blended, if necessary, in the water-in-oil emulsion sunscreen cosmetic according to the present invention. Examples thereof include a whitening agent, a moisturizing agent, an antioxidant, an oily active agent, a surfactant, an aqueous-phase-thickening agent, an alcohol, a non-spherical powder, a colorant, and an aqueous active agent. The water-in-oil emulsion sunscreen cosmetic according to the present invention can be produced by using a conventional method.

The water-in-oil emulsion sunscreen cosmetic according to the present invention can be provided, for example, as a sunscreen cream, a sunscreen emulsion, or a sunscreen lotion, and in addition, can be used as a foundation, base for makeup, makeup cosmetic, hair cosmetic, or the like, with sunscreening ability.

EXAMPLES

Hereinafter, the present invention will be described in more detail by using specific examples. However, the present invention is not limited to the following Examples. In Examples and so on in the following, blend ratios are values in mass %, unless specified otherwise.

Examples 1 to 5 and Comparative Examples 1 and 2

Oil components were heated to melt, and powders were dispersed therein. An aqueous phase separately prepared through dissolving was added thereto, and the resultant was stirred for emulsification to prepare each of the water-in-oil emulsion sunscreen cosmetics having the compositions listed in the following Table 1.

The ratio of oil-phase-thickening agents=[total quantity of component (B) and component (C)]/[total quantity of (E) non-volatile liquid oils except silicone oils] was calculated from the blend ratios of corresponding components.

Measurement of UV Protection

Each cosmetic (sample) in a quantity of 2 mg/cm$^2$ was dropped on a measurement plate (S-plate) (5×5 cm V-grooved PMMA plate, SPFMASTER-PA01), and applied thereto by the finger for 60 seconds, and dried for 15 minutes. Thereafter, the absorbance was measured with a U-3500 auto-recording spectrophotometer manufactured by Hitachi, Ltd. The absorbance (Abs) was calculated in accordance with the following equation by using glycerin, which does not absorb ultraviolet rays, as a control.

$$Abs=-\log(T/To)$$

T: transmittance of sample, To: transmittance of glycerin

The plate after measurement was sufficiently soaked in water having a hardness of 50 to 500, and in the state stirred the water for 30 minutes (with a three-one motor at 300 rpm). Thereafter, the plate was dried for approximately 15 to 30 minutes until water droplets on the surface disappeared, and then the absorbance was measured again. The Abs change rate (defined by the following equation) was calculated from the integrated values of Abs before and after the water soaking (bathing) as an indication of UV protection ability improving effect.

UV protection ability improving effect:

$$Abs\ change\ rate\ (\%) = (integrated\ value\ of\ Abs\ after\ water\ soaking)/(integrated\ value\ of\ Abs\ before\ water\ soaking) \times 100$$

In the present invention, an Abs change rate over 100(%) was defined as improvement of UV protection ability.

TABLE 1

| | Comparative Example 1 | Comparative Example 2 | Example 1 | Example 2 | Example 3 | Example 4 |
|---|---|---|---|---|---|---|
| Light isoparaffin | balance | balance | balance | balance | balance | balance |
| PEG-9 polydimethylsiloxyethyl dimethicone | 1.5 | 1.5 | 1.5 | 1.5 | 1.5 | 1.5 |
| Decamethyltetrasiloxane | 10 | 10 | 10 | 10 | 10 | 10 |
| Methylpolysiloxane (6cs) | 4 | 4 | 4 | 4 | 4 | 4 |
| Dimethyldistearammonium hectorite | — | 0.5 | 0.3 | 0.5 | 0.5 | 0.5 |
| Dextrin palmitate | — | — | 1 | 0.5 | 1 | 2 |
| Trimethylsiloxysilicate | 2 | 2 | 2 | 2 | 2 | 2 |
| Polyoxybutylene polyoxypropylene glycol | 2.5 | 2.5 | 2.5 | 2.5 | 2.5 | 2.5 |
| Isopropyl myristate | 3 | 3 | 3 | 3 | 3 | 3 |
| Octocrylene | 3 | 3 | 3 | 3 | 3 | 3 |
| Dimethicodiethyl benzalmalonate | 3 | 3 | 3 | 3 | 3 | 3 |
| 2-Ethylhexyl paramethoxycinnamate | 8 | 7 | 7 | 7 | 7 | 7 |
| 2,4-Bis-[{4-(2-ethylhexyloxy)-2-hydroxy]-phenyl}-6-(4-methoxyphenyl)-1,3,5-triazine | 1 | 1 | 1 | 1 | 1 | 1 |
| Hexyl diethylaminohydroxybenzoylbenzoate | 1 | 1 | 1 | 1 | 1 | 1 |
| Dimethicone-coated zinc oxide fine particle | 10 | 10 | 10 | 10 | 10 | 10 |
| Methylsiloxane network polymer | 5 | 5 | 5 | 5 | 5 | 5 |
| Talc | 5 | 5 | 5 | 5 | 5 | 5 |
| Purified water | 10 | 10 | 10 | 10 | 10 | 10 |
| Trisodium edetate | q.s. | q.s. | q.s. | q.s. | q.s. | q.s. |
| Glycerin | 1 | 1 | 1 | 1 | 1 | 1 |
| Xylitol | 1 | 1 | 1 | 1 | 1 | 1 |
| Ethanol | 10 | 10 | 10 | 10 | 10 | 10 |
| Total | 100 | 100 | 100 | 100 | 100 | 100 |
| Ratio of oil phase-thickening agents | 0.000 | 0.024 | 0.063 | 0.049 | 0.073 | 0.122 |
| Integrated value of Abs before water soaking | 174.8 | 170.2 | 160.1 | 180.4 | 155.5 | 153.4 |
| Integrated value of Abs after water soaking | 172.7 | 166.5 | 204.7 | 187.8 | 173.3 | 173.4 |
| Abs change rate (%) before and after water soaking | 98.8 | 97.8 | 127.9 | 104.1 | 111.5 | 113.0 |

| | Example 5 | Example 6 | Comparative Example 3 | Comparative Example 4 | Example 7 | Example 8 | Example 9 |
|---|---|---|---|---|---|---|---|
| Light isoparaffin | balance | balance | balance | balance | balance | balance | balance |
| PEG-9 polydimethylsiloxyethyl dimethicone | 1.5 | 1.5 | 1.5 | 1.5 | 1.5 | 1.5 | 1.5 |
| Decamethyltetrasiloxane | 10 | 10 | 10 | 10 | 10 | 10 | 10 |
| Methylpolysiloxane (6cs) | 4 | 4 | 4 | 4 | 4 | 4 | 4 |
| Dimethyldistearammonium hectorite | 0.5 | 0.5 | 0.5 | 0.5 | 0.5 | 0.5 | 0.5 |
| Dextrin palmitate | 3 | 1 | 1 | 1 | 5 | 7.5 | 10 |
| Trimethylsiloxysilicate | 2 | 2 | 2 | 2 | 2 | 2 | 2 |
| Polyoxybutylene polyoxypropylene glycol | 2.5 | 2.5 | 2.5 | 2.5 | 2.5 | 2.5 | 2.5 |
| Isopropyl myristate | 3 | 3 | 20 | 30 | 3 | 3 | 3 |
| Octocrylene | 3 | 3 | 3 | 3 | 3 | 3 | 3 |
| Dimethicodiethyl benzalmalonate | 3 | 3 | 3 | 3 | 3 | 3 | 3 |

TABLE 1-continued

|  | | | | | | | |
|---|---|---|---|---|---|---|---|
| 2-Ethylhexyl paramethoxycinnamate | 7 | 8 | 8 | 8 | 8 | 8 | 8 |
| 2,4-Bis-[{4-(2-ethylhexyloxy)-2-hydroxy]-phenyl}-6-(4-methoxyphenyl)-1,3,5-triazine | 1 | 1 | 1 | 1 | 1 | 1 | 1 |
| Hexyl diethylaminohydroxybenzoylbenzoate | 1 | 1 | 1 | 1 | 1 | 1 | 1 |
| Dimethicone-coated zinc oxide fine particle | 10 | 10 | 10 | 10 | 10 | 10 | 10 |
| Methylsiloxane network polymer | 5 | 5 | 5 | 5 | — | — | — |
| Talc | 5 | 5 | 5 | 5 | 10 | 10 | 10 |
| Purified water | 10 | 10 | 10 | 10 | 10 | 10 | 10 |
| Trisodium edetate | q.s. | q.s. | q.s. | q.s. | q.s. | q.s. | q.s. |
| Glycerin | 1 | 1 | 1 | 1 | 1 | 1 | 1 |
| Xylitol | 1 | 1 | 1 | 1 | 1 | 1 | 1 |
| Ethanol | 10 | 10 | 10 | 10 | 10 | 10 | 10 |
| Total | 100 | 100 | 100 | 100 | 100 | 100 | 100 |
| Ratio of oil phase-thickening agents | 0.171 | 0.070 | 0.039 | 0.031 | 0.256 | 0.372 | 0.488 |
| Integrated value of Abs before water soaking | 148.9 | 173.1 | 202.1 | 197.1 | 146.1 | 123.4 | 132.7 |
| Integrated value of Abs after water soaking | 185.9 | 202.3 | 186.3 | 171.7 | 171.3 | 141.2 | 148.7 |
| Abs change rate (%) before and after water soaking | 124.8 | 116.9 | 92.2 | 87.1 | 117.3 | 114.4 | 112.1 |

As shown in Table 1, the UV protection ability was degraded after water soaking in the case that the ratio of oil-phase-thickening agents was less than 0.04 as a result of difference in the blend ratio of component (B), component (C), or (E) non-volatile liquid oils except silicone oils, despite the fact that the blend ratio of (A) UV protective agent or (F) oil-soluble film forming agent was almost unchanged (Comparative Examples 1 to 4). In contrast, if the ratio of oil-phase-thickening agents was within the range of 0.04 or more and less than 0.68 (Examples 1 to 9), the UV protection ability increased by up to approximately 28% (Example 1) after water soaking in comparison with that before water soaking.

Example 10 and Comparative Example 5

The water-in-oil emulsion sunscreen cosmetics having compositions listed in Table 2 were prepared, and the absorbance change rate before and after water soaking was determined as described above.

The ratio of film forming agents=[total quantity of component (F)]/[total quantity of (E) non-volatile liquid oils except silicone oils] was calculated from the blend ratios of corresponding components.

TABLE 2

|  | Comparative Example 5 | Example 10 |
|---|---|---|
| Cyclomethicone | 40 | 37 |
| Glyceryl tri(2-ethylhexanoate) | 3 | 6 |
| 2-Ethylhexyl paramethoxycinnamate | 5 | 5 |
| Trimethylsiloxysilicate | 4 | 4 |
| PEG-10 dimethicone | 2 | 2 |
| Dimethyldistearammonium hectorite | 0.5 | 0.5 |
| Dextrin palmitate | 5 | 5 |
| Dimethicone-coated zinc oxide fine particle | 20 | 20 |
| Dimethicone-coated titanium oxide fine particle | 5 | 5 |
| 1,3-Butylene glycol | 5 | 5 |
| Phenoxyethanol | 0.5 | 0.5 |
| Purified water | 10 | 10 |
| Ratio of oil phase-thickening agents | 0.688 | 0.500 |
| Ratio of film forming agents | 0.500 | 0.364 |
| Integrated value of Abs before water soaking | 159.3 | 154.7 |
| Integrated value of Abs after water soaking | 157.8 | 157.1 |
| Abs change rate (%) before and after water soaking | 99.0 | 101.5 |

As shown in Table 2, the UV protection ability was degraded after water soaking in Comparative Example 5, in which the ratio of oil phase-thickening agents was 0.68 or more as a result of difference in the blend ratio of non-volatile liquid oils. In Example 10, in which the ratio was within the range specified in the present invention, on the other hand, the UV protection ability improved after water soaking in comparison with that before water soaking. In addition, a film-like feeling upon application caused and cleansability became poor in Comparative Example 5 because the ratio of film forming agents exceeds 0.5.

Examples 11 to 18 and Comparative Example 6

The water-in-oil emulsion sunscreen cosmetics having compositions listed in Tables 3 and 4 were prepared, and the absorbance change rate before and after water soaking was determined as described above.

TABLE 3

|  | Comparative Example 6 | Example 11 | Example 12 | Example 13 | Example 14 |
|---|---|---|---|---|---|
| Light isoparaffin | balance | balance | balance | balance | balance |
| PEG-9 polydimethylsiloxyethyl dimethicone | 1.5 | 1.5 | 1.5 | 1.5 | 1.5 |
| Decamethyltetrasiloxane | 10 | 10 | 10 | 10 | 10 |

TABLE 3-continued

|  | Comparative Example 6 | Example 11 | Example 12 | Example 13 | Example 14 |
|---|---|---|---|---|---|
| Methylpolysiloxane (6 cs) | 4 | 4 | 4 | 4 | 4 |
| Dimethyldistearammonium hectorite | 0.5 | 0.5 | 0.5 | 0.5 | 0.5 |
| Sucrose fatty acid ester | — | 3 | — | — | — |
| Dextrin (palmitate/ethylhexanoate) | — | — | 3 | — | — |
| Magnesium stearate | — | — | — | 3 | — |
| Calcium stearate | — | — | — | — | 0.5 |
| Trimethylsiloxysilicate | 2 | 2 | 2 | 2 | 2 |
| Polyoxybutylene polyoxypropylene glycol | 2.5 | 2.5 | 2.5 | 2.5 | 2.5 |
| Isopropyl myristate | 3 | 3 | 3 | 3 | 3 |
| Octocrylene | 3 | 3 | 3 | 3 | 3 |
| Dimethicodiethyl benzalmalonate | 3 | 3 | 3 | 3 | 3 |
| 2-Ethylhexyl paramethoxycinnamate | 7 | 7 | 7 | 7 | 7 |
| 2,4-Bis-[{4-(2-ethylhexyloxy)-2-hydroxy]-phenyl}-6-(4-methoxyphenyl)-1,3,5-triazine | 1 | 1 | 1 | 1 | 1 |
| Hexyl diethylaminohydroxybenzoylbenzoate | 1 | 1 | 1 | 1 | 1 |
| Dimethicone-coated zinc oxide fine particle | 10 | 10 | 10 | 10 | 10 |
| Methylsiloxane network polymer | 5 | 5 | 5 | 5 | — |
| Talc | 5 | 5 | 5 | 5 | 10 |
| Purified water | 10 | 10 | 10 | 10 | 10 |
| Trisodium edetate | q.s. | q.s. | q.s. | q.s. | q.s. |
| Glycerin | 1 | 1 | 1 | 1 | 1 |
| Xylitol | 1 | 1 | 1 | 1 | 1 |
| Ethanol | 10 | 10 | 10 | 10 | 10 |
| Total | 100 | 100 | 100 | 100 | 100 |
| Ratio of oil phase-thickening agents | 0.024 | 0.171 | 0.171 | 0.171 | 0.049 |
| Integrated value of Abs before water soaking | 170.2 | 188.9 | 162.5 | 185.7 | 163.8 |
| Integrated value of Abs after water soaking | 166.5 | 251.9 | 195.8 | 215.4 | 212.5 |
| Abs change rate (%) before and after water soaking | 97.8 | 133.3 | 120.4 | 116.0 | 129.8 |

TABLE 4

|  | Example 15 | Example 16 | Example 17 | Example 18 |
|---|---|---|---|---|
| Light isoparaffin | balance | balance | balance | balance |
| PEG-9 polydimethylsiloxyethyl dimethicone | 1.5 | 1.5 | 1.5 | 1.5 |
| Decamethyltetrasiloxane | 10 | 10 | 10 | 10 |
| Methylpolysiloxane (6 cs) | 4 | 4 | 4 | 4 |
| Dimethyldistearammonium hectorite | 0.5 | 0.5 | 0.5 | 0.5 |
| Stearic acid | 1 | 3 | — | — |
| Behenic acid | — | — | 5 | — |
| Myristic acid | — | — | — | 5 |
| Trimethylsiloxysilicate | 2 | 2 | 2 | 2 |
| Polyoxybutylene polyoxypropylene glycol | 2.5 | 2.5 | 2.5 | 2.5 |
| Isopropyl myristate | 3 | 3 | 3 | 3 |
| Octocrylene | 3 | 3 | 3 | 3 |
| Dimethicodiethyl benzalmalonate | 3 | 3 | 3 | 3 |
| 2-Ethylhexyl paramethoxycinnamate | 7 | 7 | 7 | 7 |
| 2,4-Bis-[{4-(2-ethylhexyloxy)-2-hydroxy]-phenyl}-6-(4-methoxyphenyl)-1,3,5-triazine | 1 | 1 | 1 | 1 |
| Hexyl diethylaminohydroxybenzoylbenzoate | 1 | 1 | 1 | 1 |
| Dimethicone-coated zinc oxide fine particle | 9 | 9 | 9 | 9 |
| Dimethicone-coated titanium oxide fine particle | 1 | 1 | 1 | 1 |
| Methylsiloxane network polymer | 5 | 5 | 5 | 5 |
| Talc | 5 | 5 | 5 | 5 |
| Purified water | 10 | 10 | 10 | 10 |
| Trisodium edetate | q.s. | q.s. | q.s. | q.s. |
| Glycerin | 1 | 1 | 1 | 1 |
| Xylitol | 1 | 1 | 1 | 1 |
| Ethanol | 10 | 10 | 10 | 10 |
| Total | 100 | 100 | 100 | 100 |
| Ratio of oil phase-thickening agents | 0.073 | 0.171 | 0.268 | 0.268 |
| Integrated value of Abs before water soaking | 155.6 | 148.6 | 135.9 | 147.2 |

TABLE 4-continued

|  | Example 15 | Example 16 | Example 17 | Example 18 |
|---|---|---|---|---|
| Integrated value of Abs after water soaking | 166.3 | 160.6 | 146.8 | 157.7 |
| Abs change rate (%) before and after water soaking | 106.8 | 108.0 | 108.0 | 107.1 |

As shown in Tables 3 and 4, a UV protection ability higher than that before water soaking was achieved after water soaking even in the case that the type of the oil-phase-thickening agent (component (C)) changed (Examples 11 to 18). In the case that component (C) was not blended, on the other hand, the UV protection ability was degraded after water soaking (Comparative Example 6).

Examples 19 to 23 and Comparative Examples 7 to 12

The water-in-oil emulsion sunscreen cosmetics having compositions listed in Tables 5 and 6 were prepared, and the absorbance change rate before and after water soaking was determined as described above.

TABLE 5

|  | Example 19 | Example 20 | Example 21 | Example 22 |
|---|---|---|---|---|
| Light isoparaffin | balance | balance | balance | balance |
| PEG-9 polydimethylsiloxyethyl dimethicone | 1.5 | — | — | — |
| Lauryl PEG-9 polydimethylsiloxyethyl dimethicone | — | 1.5 | — | — |
| PEG-10 dimethicone | — | — | 1.5 | — |
| cetylPEG/PPG-10/1 dimethicone | — | — | — | 1.5 |
| Bis-butyldimethicone polyglyceryl-3 | — | — | — | — |
| Diglyceryl diisostearate | — | — | — | — |
| PEG-10 methyl ether dimethicone | — | — | — | — |
| PEG-12 dimethicone | — | — | — | — |
| PEG-8 diisostearate | — | — | — | — |
| Sorbitan sesquiisostearate | — | — | — | — |
| Sorbitan tristearate | — | — | — | — |
| Decamethyltetrasiloxane | 10 | 10 | 10 | 10 |
| Methylpolysiloxane (6 cs) | 4 | 4 | 4 | 4 |
| Dimethyldistearammonium hectorite | 0.5 | 0.5 | 0.5 | 0.5 |
| Dextrin palmitate | 1 | 1 | 1 | 1 |
| Trimethylsiloxysilicate | 2 | 2 | 2 | 2 |
| Polyoxybutylene polyoxypropylene glycol | 2.5 | 2.5 | 2.5 | 2.5 |
| Isopropyl myristate | 3 | 3 | 3 | 3 |
| Octocrylene | 3 | 3 | 3 | 3 |
| Dimethicodiethyl benzalmalonate | 3 | 3 | 3 | 3 |
| 2-Ethylhexyl paramethoxycinnamate | 8 | 8 | 8 | 8 |
| 2,4-Bis-[{4-(2-ethylhexyloxy)-2-hydroxy]-phenyl}-6-(4-methoxyphenyl)-1,3,5-triazine | 1 | 1 | 1 | 1 |
| Hexyl diethylaminohydroxybenzoylbenzoate | 1 | 1 | 1 | 1 |
| Dimethicone-coated zinc oxide fine particle | 9 | 9 | 9 | 9 |
| Methylsiloxane network polymer | 5 | 5 | 5 | 5 |
| Talc | 5 | 5 | 5 | 5 |
| Purified water | 10 | 10 | 10 | 10 |
| Trisodium edetate | q.s. | q.s. | q.s. | q.s. |
| Glycerin | 1 | 1 | 1 | 1 |
| Xylitol | 1 | 1 | 1 | 1 |
| Ethanol | 10 | 10 | 10 | 10 |
| Total | 100 | 100 | 100 | 100 |
| Ratio of oil phase-thickening agents | 0.070 | 0.070 | 0.070 | 0.070 |
| HLB of activating agent, (D) | 4.0 | 3.0 | 2 | 5.0 |
| Integrated value of Abs before water soaking | 163.0 | 166.7 | 158.0 | 153.1 |
| Integrated value of Abs after water soaking | 188.7 | 181.9 | 186.1 | 168.5 |
| Abs change rate (%) before and after water soaking | 115.8 | 109.1 | 117.8 | 110.0 |

TABLE 6

|  | Example 23 | Comparative Example 7 | Comparative Example 8 | Comparative Example 9 | Comparative Example 10 | Comparative Example 11 | Comparative Example 12 |
|---|---|---|---|---|---|---|---|
| Light isoparaffin | balance | balance | balance | balance | balance | balance | balance |
| PEG-9 polydimethylsiloxyethyl dimethicone | — | — | — | — | — | — | — |
| Lauryl PEG-9 polydimethylsiloxyethyl dimethicone | — | — | — | — | — | — | — |
| PEG-10 dimethicone | — | — | — | — | — | — | — |
| CetylPEG/PPG-10/1 dimethicone | — | — | — | — | — | — | — |
| Bis-butyldimethicone polyglyceryl-3 | 1.5 | — | — | — | — | — | — |

TABLE 6-continued

|  | Example 23 | Comparative Example 7 | Comparative Example 8 | Comparative Example 9 | Comparative Example 10 | Comparative Example 11 | Comparative Example 12 |
|---|---|---|---|---|---|---|---|
| Diglyceryl diisostearate | — | 1.5 | — | — | — | — | — |
| PEG-10 methyl ether dimethicone | — | — | 1.5 | — | — | — | — |
| PEG-12 dimethicone | — | — | — | 1.5 | — | — | — |
| PEG-8 diisostearate | — | — | — | — | 1.5 | — | — |
| Sorbitan sesquiisostearate | — | — | — | — | — | 1.5 | — |
| Sorbitan tristearate | — | — | — | — | — | — | 1.5 |
| Decamethyltetrasiloxane | 10 | 10 | 10 | 10 | 10 | 10 | 10 |
| Methylpolysiloxane (6cs) | 4 | 4 | 4 | 4 | 4 | 4 | 4 |
| Dimethyldistearammonium hectorite | 0.5 | 0.5 | 0.5 | 0.5 | 0.5 | 0.5 | 0.5 |
| Dextrin palmitate | 1 | 1 | 1 | 1 | 1 | 1 | 1 |
| Trimethylsiloxysilicate | 2 | 2 | 2 | 2 | 2 | 2 | 2 |
| Polyoxybutylene polyoxypropylene glycol | 2.5 | 2.5 | 2.5 | 2.5 | 2.5 | 2.5 | 2.5 |
| Isopropyl myristate | 3 | 3 | 3 | 3 | 3 | 3 | 3 |
| Octocrylene | 3 | 3 | 3 | 3 | 3 | 3 | 3 |
| Dimethicodiethyl benzalmalonate | 3 | 3 | 3 | 3 | 3 | 3 | 3 |
| 2-Ethylhexyl paramethoxycinnamate | 8 | 8 | 8 | 8 | 8 | 8 | 8 |
| 2,4-Bis-[{4-(2-ethylhexyloxy)-2-hydroxy]-phenyl}-6-(4-methoxyphenyl)-1,3,5-triazine | 1 | 1 | 1 | 1 | 1 | 1 | 1 |
| Hexyl diethylaminohydroxybenzoylbenzoate | 1 | 1 | 1 | 1 | 1 | 1 | 1 |
| Dimethicone-coated zinc oxide fine particle | 9 | 9 | 9 | 9 | 9 | 9 | 9 |
| Methylsiloxane network polymer | — | — | — | — | — | — | — |
| Talc | 10 | 10 | 10 | 10 | 10 | 10 | 10 |
| Purified water | 10 | 10 | 10 | 10 | 10 | 10 | 10 |
| Trisodium edetate | q.s. | q.s. | q.s. | q.s. | q.s. | q.s. | q.s. |
| Glycerin | 1 | 1 | 1 | 1 | 1 | 1 | 1 |
| Xylitol | 1 | 1 | 1 | 1 | 1 | 1 | 1 |
| Ethanol | 10 | 10 | 10 | 10 | 10 | 10 | 10 |
| Total | 100 | 100 | 100 | 100 | 100 | 100 | 100 |
| Ratio of oil phase-thickening agents | 0.070 | 0.070 | 0.070 | 0.070 | 0.070 | 0.070 | 0.070 |
| HLB of activating agent (D) | 0.5 | 2.0 | 14 | 8 | 5 | 4.5 | 2.1 |
| Integrated value of Abs before water soaking | 153.3 | 164.8 | 170.9 | 175.3 | 147.9 | 157.8 | 167.9 |
| Integrated value of Abs after water soaking | 185.1 | 159.8 | 139.8 | 138.7 | 92.0 | 103.9 | 143.8 |
| Abs change rate (%) before and after water soaking | 120.7 | 97.0 | 81.8 | 79.1 | 62.3 | 65.8 | 85.7 |

As shown in Tables 5 and 6, the UV protection ability was degraded after water soaking in the case that a surfactant other than the silicone-based surfactant was used (Comparative Examples 7 and 10 to 12), and in the case that a silicone-based surfactant having an HLB of 8 or more was used (Comparative Examples 8 and 9). In contrast, in the case that a silicone-based surfactant having an HLB of less than 8 was used, the UV protection ability improved after water soaking in comparison with that before water soaking.

Examples 24 to 27

The water-in-oil emulsion sunscreen cosmetics having compositions listed in Table 7 below were prepared, and the absorbance change rate before and after water soaking was determined as described above.

TABLE 7

|  | Example 24 | Example 25 | Example 26 | Example 27 |
|---|---|---|---|---|
| Light isoparaffin | balance | balance | balance | balance |
| Polyoxyethylene-methylpolysiloxane copolymer | 1.5 | 1.5 | 1.5 | 1.5 |
| Decamethyltetrasiloxane | 10 | 10 | 10 | 10 |
| Methylpolysiloxane (6 cs) | 4 | 4 | 4 | 4 |
| Dimethyldistearammonium hectorite | 0.5 | 0.5 | 0.5 | 0.5 |
| Dextrin palmitate | 1 | 1 | 5 | 7.5 |
| Trimethylsiloxysilicate | 0.4 | 2 | 3 | 5 |
| Polyoxybutylene polyoxypropylene glycol | 2.5 | 2.5 | 2.5 | 2.5 |
| Isopropyl myristate | 3 | 3 | 3 | 3 |
| Octocrylene | 3 | 3 | 3 | 3 |
| 2-Ethylhexyl paramethoxycinnamate | 8 | 8 | 8 | 8 |
| 2,4-Bis-[{4-(2-ethylhexyloxy)-2-hydroxy]-phenyl}-6-(4-methoxyphenyl)-1,3,5-triazine | 1 | 1 | 1 | 1 |
| Hexyl diethylaminohydroxybenzoylbenzoate | 1 | 1 | 1 | 1 |
| Dimethicone-coated zinc oxide fine particle | 10 | 10 | 10 | 10 |
| Methylsiloxane network polymer | 5 | 5 | — | — |
| Talc | 5 | 5 | 10 | 10 |
| Purified water | 10 | 10 | 10 | 10 |
| Trisodium edetate | q.s. | q.s. | q s. | q.s. |

TABLE 7-continued

|  | Example 24 | Example 25 | Example 26 | Example 27 |
|---|---|---|---|---|
| Glycerin | 1 | 1 | 1 | 1 |
| Xylitol | 1 | 1 | 1 | 1 |
| Ethanol | 10 | 10 | 10 | 10 |
| Total | 100 | 100 | 100 | 100 |
| Ratio of oil phase-thickening agents | 0.081 | 0.081 | 0.297 | 0.432 |
| Ratio of film forming agents | 0.014 | 0.070 | 0.105 | 0.175 |
| Integrated value of Abs before water soaking | 142.9 | 157.8 | 161.3 | 171.6 |
| Integrated value of Abs after wate soak ng | 157.6 | 189.7 | 181.4 | 193.1 |
| Abs change rate (%) before and after water soaking | 110.3 | 120.2 | 112.4 | 112.5 |

As shown in Table 7, the UV protection ability improved after water soaking in comparison with that before water soaking in the case that the ratio of oil-phase-thickening agents was within the range specified in the present invention, despite the fact that the blend ratios of components (C) and (E) changed. Further, the cosmetics in these Examples were excellent in texture and cleansability.

Example 28

The water-in-oil emulsion sunscreen cosmetics having a composition listed in Table 8 below were prepared, and the absorbance change rate before and after water soaking was determined as described above.

TABLE 8

|  | Example 28 |
|---|---|
| Ion-exchanged water | balance |
| Dynamite glycerin | 5 |
| 1,3-Butylene glycol | 5 |
| Dimethyldistearammonium hectorite | 0.2 |
| Stearic acid (derived from plant oil) | 0.01 |
| Aluminum stearate | 0.9 |
| Dextrin palmitate | 0.01 |
| Dimethylpolysiloxane-polyethylene glycol copolymer | 2.5 |
| PEG-9 polydimethylsiloxyethyl dimethicone | 2 |
| Bis-butyldimethicone polyglyceryl-3 | 1 |
| Decamethyltetrasiloxane | 22 |
| Methylpolysiloxane | 3 |
| Diisopropyl sebacate | 5 |
| Hydrogenated polydecene | 5 |
| Isostearic acid | 0.5 |
| Cyclomethicone/Trimethylsiloxysilicate | 1 |
| Titanium oxide | 10 |
| Zinc oxide | 20 |
| Spherical powder of polymethyl methacrylate | 5 |
| PEG/PPG-14/7 dimethyl ether | 0.5 |
| Sodium hexametaphosphate | q.s. |
| Ratio of oil phase-thickening agents | 0.110 |
| Integrated value of Abs before water soaking | 167.5 |
| integrated value of Abs after water soaking | 203.2 |
| Abs change rate (%) before and after water soaking | 121.3 |

As shown in Table 8, the effect of improving UV protection ability after water soaking in comparison with that before water soaking, which is an effect unique to the present invention, was achieved even in the case that (A) UV protective agent consisted only of UV scattering agents (containing no organic UV absorbing agent).

Formulation Examples of the water-in-oil emulsion sunscreen cosmetic according to the present invention are listed below. Needless to say, the present invention is not limited to these Formulation Examples, but specified by the appended claims. Each of the blend ratios is a value in mass % based on the total quantity of the water-in-oil emulsion sunscreen cosmetic.

Formulation Example 1. Sunscreen Cream

| (Component name) | Blend ratio (%) |
|---|---|
| Purified water | balance |
| Ethanol | 8 |
| Xylitol | 1 |
| Glycerin | 2 |
| 1,3-butylene glycol | 5 |
| Lauryl PEG-9 polydimethylsiloxyethyl dimethicone | 3 |
| 3-(10-carboxydecyl)-1,1,1,3,5,5,5-heptamethyltrisiloxane | 1 |
| Tetraisobutane | 6 |
| Light isoparaffin | 4 |
| Methylpolysiloxane | 6 |
| Isopropyl myristate | 5 |
| Trimethylsiloxysilicate | 3 |
| 2-Ethylhexyl paramethoxycinnamate | 7 |
| Octocrylene | 3 |
| Dimethyldistearammonium hectorite | 2 |
| Stearic acid | 1 |
| Dextrin palmitate | 2 |
| Polyoxyethylene(14) polyoxypropylene(7) dimethyl ether | 0.5 |
| Zinc oxide | 20 |
| Titanium oxide | 2 |
| Polymethyl methacrylate | 5 |
| Methylsiloxane network polymer | 2 |
| Talc | 1 |
| Silicic anhydride | 1 |
| Trisodium edetate | q.s. |
| Phenoxyethanol | q.s. |
| Fragrance | q.s. |

Formulation Example 2. Sunscreen Emulsion

| (Component name) | Blend ratio (%) |
|---|---|
| Purified water | balance |
| Ethanol | 5 |
| Glycerin | 1 |
| 1,3-Butylene glycol | 5 |
| Polyoxyethylene methylglucoside | 2 |
| Polyoxyethylene-methylpolysiloxane copolymer | 2.5 |
| Tetraisobutane | 5 |
| Light isoparaffin | 5 |
| Methylpolysiloxane | 5 |
| Cetyl 2-ethylhexanoate | 1 |
| Isostearic acid | 1 |
| Isopropyl myristate | 8 |

-continued

| (Component name) | Blend ratio (%) |
| --- | --- |
| Trimethylsiloxysilicate | 4 |
| 2-Ethylhexyl paramethoxycinnamate | 5 |
| Octocrylene | 5 |
| Dimethyldistearammonium heotorite | 0.2 |
| Stearic acid | 0.3 |
| Dextrin palmitate | 0.4 |
| Polyoxyethylene(14) polyoxypropylene(7) dimethyl ether | 0.3 |
| Zinc oxide | 20 |
| Titanium oxde | 2 |
| Polymethyl methacrylate | 4 |
| Trisodium edetate | q.s. |
| Phenoxyethanol | q.s. |
| Fragrance | q.s. |

Formulation Example 3. Sunscreen Emulsion

| (Component name) | Blend ratio (%) |
| --- | --- |
| Ion-exchanged water | balance |
| Ethanol | 5 |
| Glycerin | 2 |
| 1,3-butylene glycol | 5 |
| Xylitol | 1 |
| Lauryl PEG-9 polydimethylsiloxyethyl dimethicone | 3 |
| Tetraisobutane | 5 |
| Light isoparaffin | 5 |
| Methylpolysiloxane | 3 |
| Glyceryl tri(2-ethylhexanoate) | 5 |
| Diisopropyl sebacate | 10 |
| Polyoxybutylene polyoxypropylene glycol | 2 |
| Trimethylsiloxysilicate | 3 |
| Octocrylene | 5 |
| 2,4-Bis-[{4-(2-ethylhexyloxy)-2-hydroxy]-phenyl}-6-(4-methoxyphenyl)-1,3,5-triazine | 1 |
| 4-tert-Butyl-4'-methoxydibenzoylmethane | 2 |
| Oxybenzone | 2 |
| Dextrin palmitate | 0.2 |
| Sucrose fatty acid ester | 1 |
| Stearic acid | 0.1 |
| Polyoxyethylene(14) polyoxypropylene(7) dimethyl ether | 0.2 |
| Dimethyldistearammonium hectorite | 1 |
| Titanium oxide | 6 |
| Methylsiloxane network polymer | 6 |
| Disodium edetate | q.s. |
| Phenoxyethanol | q.s. |
| Fragrance | q.s. |

Formulation Example 4. Sunscreen Emulsion

| (Component name) | Blend ratio (%) |
| --- | --- |
| Ion-exchanged water | balance |
| Ethanol | 10 |
| PEG-9 polydimethylsiloxyethyl dimethicone | 1.5 |
| Stearic acid | 0.3 |
| Dimethyldistearammonium hectorite | 0.5 |
| Dextrin palmitate | 2 |
| Dodecamethylcyclohexasiloxane | 10 |
| Light liquid isoparaffin | 10 |
| Methylpolysiloxane | 5 |
| Diisopropyl sebacate | 1 |

-continued

| (Component name) | Blend ratio (%) |
| --- | --- |
| Polyoxybutylene polyoxypropylene glycol | 1 |
| Isopropyl myristate | 5 |
| Isostearic acid | 0.7 |
| Trimethylsiloxysilicate | 3 |
| 2-Ethylhexyl paramethoxycinnamate | 8 |
| Octocrylene | 2 |
| 2,4-Bis-[{4-(2-ethylhexyloxy)-2-hydroxy]-phenyl}-6-(4-methoxyphenyl)-1,3,5-triazine | 2 |
| Hexyl diethylaminohydroxybenzoylbenzoate | 1 |
| Zinc oxide | 11 |
| Titanium oxide | 2 |
| Polymethyl methacrylate | 5 |
| Crosslinked silicone-network silicone block copolymer | 5 |
| Trisodium edetate | q.s. |
| Fragrance | q.s. |

Formulation Example 5. W/O Base for Makeup

| (Component name) | Blend ratio (%) |
| --- | --- |
| Dimethicone | balance |
| Water | 24 |
| Ethanol | 10 |
| Zinc oxide | 10 |
| Diisopropyl sebacate | 5 |
| Isododecane | 4 |
| Polymethyl methacrylate | 4 |
| (Vinyldimethicone/methicone silsesquioxane) crosspolymer | 3 |
| Caprylyl methicone | 3 |
| Ethylhexyl methoxycinnamate | 3 |
| Talc | 3 |
| Titanium oxide | 1.5 |
| Trifluoroalkyldimethyltrimethyl-siloxysilicate | 1.2 |
| PEG-9 polydimethylsiloxyethyl dimethicone | 1 |
| Glycerin | 1 |
| Bis-ethylhexyloxyphenol methoxyphenyl triazine | 0.5 |
| Hexyl diethylaminohydroxy-benzoylbenzoate | 0.5 |
| Dextrin palmitate | 0.5 |
| Isostearic acid | 0.5 |
| Trisodium edetate | q.s. |
| Dibutylhydroxytoluene | q.s. |
| Tocopherol | q.s. |
| Iron oxide | q.s. |

The invention claimed is:
1. A water-in-oil emulsion sunscreen cosmetic comprising:
(A) 6 to 40 mass % of a UV protective agent consisting of titanium dioxide and zinc oxide;
(B) 0.1 to 3 mass % of dimethyldistearylammonium hectorite;
(C) 0.5 to 10 mass % of an oil-phase-thickening agent, consisting of at least one compound selected from the group consisting of dextrin palmitate, stearic acid and aluminum stearate;
(D) 0.1 to 8 mass % of a silicone-based surfactant having an HLB of less than 8 consisting of at least one surfactant selected from the group consisting of PEG-10 dimethicone, PEG-9 polydimethylsiloxiethyldimethicone, and bis-butldimethicone polygryceryl-3;
(E) one or more non-volatile liquid oils other than silicone oils; and

(F) polyoxyethylene-polyoxypropylene dialkyl ether;
wherein the ratio, [total quantity of component (B) and component (C)]/[total quantity of component (E)], is 0.04 or more and less than 0.68.

2. The water-in-oil emulsion sunscreen cosmetic, according to claim 1, wherein: two or more kinds of the (C) oil-phase-thickening agents are blended.

* * * * *